United States Patent [19]
George et al.

[11] Patent Number: 6,007,794
[45] Date of Patent: Dec. 28, 1999

[54] CLEAR AEROSOL HAIR SPRAY FORMULATIONS CONTAINING A SULFOPOLYESTER IN A HYDROALCOHOLIC LIQUID VEHICLE

[75] Inventors: Scott E. George; Vicki L. Underwood, both of Kingsport; D. Michael Garber, Jonesborough; Andy H. Singleton, Kingsport, all of Tenn.

[73] Assignee: Eastman Chemical Company, Kingsport, Tenn.

[21] Appl. No.: 09/212,747

[22] Filed: Dec. 16, 1998

Related U.S. Application Data

[63] Continuation of application No. 08/852,504, May 7, 1997, Pat. No. 5,853,701, which is a continuation of application No. 08/254,011, Jun. 3, 1994, Pat. No. 5,674,479, which is a continuation of application No. 08/081,897, Jun. 25, 1993, abandoned, which is a continuation of application No. 08/523,312, Sep. 5, 1995, Pat. No. 5,660,816, which is a continuation of application No. 08/254,010, Jun. 3, 1994, Pat. No. 5,662,893.

[51] Int. Cl.[6] ...................................................... A61K 7/11
[52] U.S. Cl. .................. 424/47; 424/70.11; 424/DIG. 1; 424/DIG. 2; 424/45; 514/957; 132/210
[58] Field of Search ..................... 424/70.11, 45, 424/47, 70.15, 70.16, DIG. 1, DIG. 2; 514/957; 132/210

[56] References Cited

U.S. PATENT DOCUMENTS

| | | | |
|---|---|---|---|
| 4,300,580 | 11/1981 | O'Neill et al. | 132/7 |
| 4,897,262 | 1/1990 | Nandagiri et al. | 424/70.11 |
| 5,021,238 | 6/1991 | Martino et al. | 424/DIG. 2 |
| 5,094,838 | 3/1992 | Benson et al. | 424/DIG. 1 |
| 5,126,126 | 6/1992 | Varaprath et al. | 424/47 |
| 5,158,762 | 10/1992 | Pierce | 424/47 |
| 5,164,177 | 11/1992 | Bhatt et al. | 424/47 |
| 5,176,898 | 1/1993 | Goldberg et al. | 424/47 |
| 5,266,303 | 11/1993 | Myers et al. | 424/47 |
| 5,266,308 | 11/1993 | Lee et al. | 424/70.11 |
| 5,614,173 | 3/1997 | Ulmer et al. | 424/47 |
| 5,662,893 | 9/1997 | George et al. | 424/70.11 |

FOREIGN PATENT DOCUMENTS 95 00105  1/1995  WIPO.

OTHER PUBLICATIONS

Martino, G. T et al. (1992). Spray Technology & Marketing, Mar. Issue, pp. 34–39.

Johnsen, M.A. Spray Technology & Marketing, Jun. Issue, pp. 32–40.

*Primary Examiner*—Raj Bawa
*Attorney, Agent, or Firm*—Jonathan D. Wood; Harry J. Gwinnell

[57] ABSTRACT

This invention relates to an aerosol hair spray formulation containing 0.5 to 15 weight percent of a water-dispersible or water-dissipatible, linear sulfopolyester having a Tg of 40° C. to 50° C. and an inherent viscosity of 0.24 to 0.60 dl/g which contains repeat units from 20 to 26 mole percent dimethyl-5-sodiosulfoisophthalate and 74 to 80 mole percent isophthalic acid, based on 100 mole percent dicarboxylic acid; 10 to 30 mole percent 1,4-cyclohexanedimethanol and 70 to 90 percent diethylene glycol, based on 100 mole percent diol; and up to 60 weight percent of an alcohol. The aerosol hair spray formulations are clear, have improved dry time and curl retention, and exhibit less than 20 NTU's, which is a measure of turbidity, even at high concentrations of alcohol.

19 Claims, No Drawings

CLEAR AEROSOL HAIR SPRAY FORMULATIONS CONTAINING A SULFOPOLYESTER IN A HYDROALCOHOLIC LIQUID VEHICLE

CROSS REFERENCE TO RELATED APPLICATIONS

The present application is a continuation of application Ser. No. 08/852,504 filed May 7, 1997, now U.S. Pat. No. 5,853,701, which is a continuation of application Ser. No. 08/254,011, now filed Jun. 3, 1994, U.S. Pat. No. 5,674,479, which is a continuation-in-part of application Ser. No. 08/081,897, filed Jun. 25, 1993, now abandoned and also a continuation of application Ser. No. 08/523,312, filed Sep. 5, 1995, now U.S. Pat. No. 5,660,816, and a continuation of Ser. No. 08/254,010, filed Jun. 3, 1994 now U.S. Pat. No. 5,662,893.

FIELD OF THE INVENTION

This invention relates to an aerosol hair spray formulation containing 0.5 to 15 weight percent of a water-dispersible or water-dissipatible, linear sulfopolyester having a Tg of 40° C. to 50° C. and an inherent viscosity of 0.24 to 0.60 dl/g which contains repeat units from 20 to 26 mole percent dimethyl-5-sodiosulfoisophthalate and 74 to 80 mole percent isophthalic acid, based on 100 mole percent dicarboxylic acid; 10 to 30 mole percent 1,4-cyclohexanedimethanol and 70 to 90 mole percent diethylene glycol, based on 100 mole percent diol; and up to 60 weight percent of an alcohol. The aerosol hair spray formulations are clear, have improved dry time and curl retention, and exhibit less than 20 NTU's, which is a measure of turbidity, even at high concentrations of alcohol.

BACKGROUND OF THE INVENTION

Hair sprays provide human hair with a particular shape or configuration and function by applying a thin film of a resin or gum onto the hair to adhere adjacent hairs together so that they retain the particular shape or configuration at the time of application.

U.S. Pat. No. 5,164,177 discloses a hair spray formulation containing 2–40% of a linear polymer including at least one vinyl or acrylate monomer, a water-soluble electrolyte, 30–90% water, and 0–30% alcohol. The water-soluble electrolyte is added to lower the viscosity of the composition to achieve a higher percentage of polymer in the composition. Such formulations, however, have poor humidity resistance, hold and curl retention.

U.S. Pat. No. 4,300,580 discloses hair spray formulations containing a water-dispersible or water-dissipatible linear sulfopolyester fixative in a water/alcohol mixture. The diol component of the sulfopolyester contains at least 20 mole percent poly(ethylene glycol). Such formulations are fast drying and have good hair holding properties but possess the disadvantage of being very difficult to remove from the hair. For example, prolonged washing is required to completely remove the water-dispersible, linear polyester fixative to obtain hair with no tacky or sticky feel. U.S. Pat. No. 4,300,580 suggests adding other substances such as poly(alkylene ether) to increase the hardness and reduce the tackiness of the formulations. However, when such formulations containing a combination of the poly(alkylene glycol) and sulfopolyester are applied to hair and allowed to dry, the fixative causes a matting of the hair. Such matting hinders combing, brushing and styling of hair.

U.S. Pat. No. 5,266,303 discloses hair spray formulations containing a water-dispersible sulfopolyester having a glass transition temperature of 36° C. to 40° C., a water-soluble polyvinyl lactam polymer, and water. The performance characteristics of such formulations are good. However, the drying time is too long, and the addition of alcohol, which would improve dry time, causes the formulations to become cloudy. Thus, the use of alcohol is not an option for improving the dry time of such formulations.

U.S. Pat. No. 5,158,762, discloses hair spray compositions containing a blend of a sulfopolyester and a water-soluble polymer in water. The sulfopolyester contains at least 40 mole percent 1,4-cyclohexanedimethanol. The performance characteristics of such formulations are good, however, the drying time is too long, and the addition of alcohol, which would improve dry time, causes the formulations to become cloudy. Thus, the use of alcohol is not an option for improving the dry time of such formulations.

U.S. Pat. No. 5,266,308 discloses aqueous hair spray compositions which contain a sulfopolyester, a water-soluble polymeric resin and a homopolymer of polyvinylpyrrolidone. The performance characteristics of such formulations are good, however, the drying time is too long, and the addition of alcohol, which would improve dry time, causes the formulations to become cloudy. Thus, the use of alcohol is not an option for improving the dry time of such formulations.

In contrast, the present inventors have unexpectedly determined that aerosol hair spray formulations which are clear and provide properties considered desirable for hair preparation such as fine spray patterns, fast drying times, prolonged curl retention under humid conditions, good holding power and resistance to build-up may be prepared with as much as 60 weight percent alcohol to facilitate rapid drying on the hair. The hair spray formulations of the present invention are clear and exhibit less than 20 NTU's which is a measure of turbidity. In the cosmetic field greater than 20 NTU's is characteristic of a cloudy mixture that is visible to the eye.

SUMMARY OF THE INVENTION

Accordingly, it is one object to the present invention to provide a clear aerosol hair spray formulation.

It is another object of the invention to provide a aerosol hair spray formulation which is not tacky, has a fast drying rate, acceptable body, consistency and exhibits improved curl retention.

Another object of the invention is to provide a aerosol hair spray formulation which is clear and has excellent storage stability and which does not clog the exit port of a aerosol container.

These and other objects are accomplished herein by an aerosol hair spray formulation having improved dry time and curl retention and exhibiting less than 20 NTU's as a measure of clarity which comprises:

(1) a sulfopolyester having a Tg of 40° C. to 50° C. and an inherent viscosity of 0.24 to 0.60 dl/g which consists essentially of repeat units from
  (a) a dicarboxylic acid component consisting essentially of 20 to 26 mole percent dimethyl-5-sodiosulfoisophthalate and 74 to 80 mole percent isophthalic acid, based on 100 mole percent dicarboxylic acid,
  (b) a diol component consisting essentially of 10 to 30 mole percent 1,4-cyclohexanedimethanol and 70 to 90 mole percent diethylene glycol, based on 100 mole percent diol;

(2) a water/alcohol liquid vehicle; and (3) 3 to 60 weight percent based on the weight of components (1), (2), and (3) of a propellant selected from the group consisting of a $C_1$–$C_4$ aliphatic hydrocarbon, dimethyl ether, and mixtures thereof, provided the sulfopolyester, component (1), is present in an amount of 0.5 to 15 weight percent, based on the total weight of the aerosol hair spray formulation.

DESCRIPTION OF THE INVENTION

The aerosol hair sprays of the present invention exhibit less than 20 NTU's which is a measure of the turbidity of a mixture. In the cosmetic field greater than 20 NTU's is characteristic of a cloudy mixture that is visible to the eye. The clear aerosol hair spray formulations of this invention contain a sulfopolyester, component (1), in an amount of 0.5 to 15 weight percent, preferably 3 to 10 weight percent, and more preferably 5 to 8 weight percent, based on the total weight of the aerosol hair spray formulation.

The sulfopolyester, component (1), has a glass transition temperature of 40° C. to 50° C. and contains repeat units from a dicarboxylic acid, a diol and a difunctional sulfomonomer. The dicarboxylic acid component of the sulfopolyester contains 20 to 26 mole percent of dimethyl-5-sodiosulfoisophthalate and 74 to 80 mole percent isophthalic acid, based on 100 mole percent dicarboxylic acid. The diol component of the sulfopolyester contains 10 to 30 mole percent 1,4-cyclohexanedimethanol and 70 to 90 mole percent diethylene glycol, based on 100 mole percent diol. The sulfopolyester has an inherent viscosity (I.V.) of 0.24 to 0.60 dl/g.

Component (2) of the aerosol hair spray is a liquid vehicle. The liquid vehicle may be water or a water/alcohol mixture. Distilled or deionized water are the preferred sources of water since tap water generally contains ions which may precipitate the sulfopolyester, component (1). If a water/alcohol mixture is used, the amount of volatile organic components which include the alcohol and propellant cannot exceed 60% of the aerosol hair spray formulation. Therefore, at least 40% of the formulation is water and the remaining 60% is alcohol and propellant. Preferably a water/alcohol mixture is used wherein the alcohol is present in an amount of 20 to 30 weight percent based on the weight of the aerosol hair spray formulation. The alcohol provides faster drying of the formulation on hair as compared to formulations prepared with only water as the liquid vehicle. The alcohol is an aliphatic straight or branched chain monohydric alcohol having 2 to 4 carbon atoms. Isopropanol and ethanol are the preferred alcohols.

The aerosol hair spray formulations of the present invention require a propellant, component (3). The propellant can be any liquefiable gas conventionally used for aerosol containers. Examples of materials that are suitable for use as propellants are trichlorofluoromethane, dichlorodifluoromethane, dichlorotetrafluoroethane, monochlorodifluoromethane, trichlorotrifluoroethane, dimethyl ether, methane, ethane, propane, n-butane and isobutane, used singly, or admixed. Water-soluble gases such as a dimethyl ether, carbon dioxide, and/or nitrous oxide also can be used to obtain aerosols having reduced flammability.

Other insoluble, compressed gases such as nitrogen, helium and fully-fluorinated oxetanes and oxepanes also are useful to deliver the formulations from aerosol containers. Other means of delivery of the above-described aqueous styling aid formulations include, aerosol sprayers, all forms of bag-in-can devices, in situ carbon dioxide ($CO_2$) generator systems, compressors, and the like.

Preferably, the propellant is either a $C_1$–$C_4$ aliphatic hydrocarbon or dimethyl ether. A preferred aliphatic hydrocarbon propellant is a mixture containing about 83 percent isobutane and about 17 percent propane. The amount of the propellant is governed by normal factors well known in the aerosol art. The level of propellant is generally from about 3% to about 60%, preferably from 5% to 45%, of the aerosol hair spray formulation. In the case where a $C_1$–$C_4$ aliphatic hydrocarbon is used as the propellant, generally about 3 to about 10 weight percent, preferably 4 to 7 weight percent, is employed. In the case where dimethyl ether is used as the propellant, generally, about 20 to about 40 weight percent, preferably, 30 to 35 weight percent, is employed. If a propellant such as dimethyl ether utilizes a vapor pressure suppressant (e.g., trichloroethane or dichloromethane), for weight percentage calculations, the amount of suppressant is included as part of the propellant.

The aerosol hair spray formulations may optionally contain a water-soluble polymer or resin, component (4). The water-soluble polymer must be soluble or dispersible in liquid vehicle, component (2). The term "water-soluble" refers to any material that has solubility of at least 1 gram per 100 grams of water, i.e. 1%, preferably a solubility of at least 5% by weight. Conversely, the term "water-insoluble" refers to substances that are insoluble at a level of less than 1 gram per 100 grams of water, i.e., less than 1% by weight. Solubility or dispersibility is determined at ambient condition (e.g., a temperature of about 25° C. and atmospheric pressure).

Water-soluble polymers useful in the formulations of the present invention are homopolymers or copolymers that can be rendered dispersible or soluble in aqueous or water/alcohol mixtures. The water-soluble polymer is a synthetic, linear, homopolymer or random copolymer including at least one, and preferably two or more vinyl or acrylate monomers of the following group: Alkyl vinyl ethers

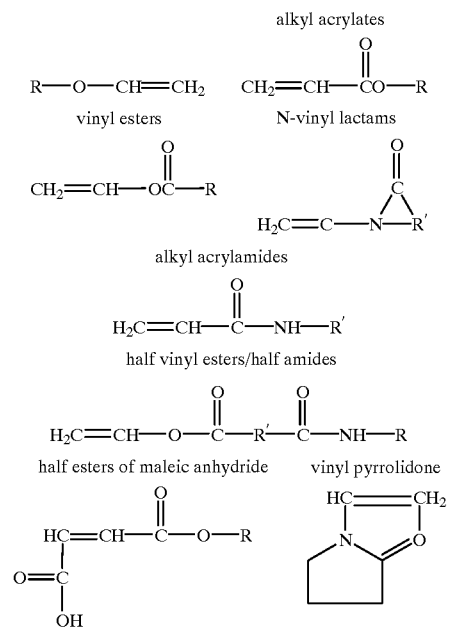

-continued

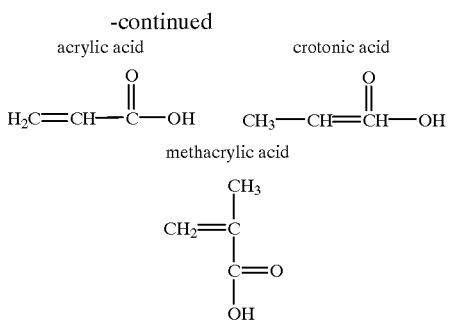

acrylic acid crotonic acid methacrylic acid

In the above formulas, R is a $C_1$ to $C_{10}$ alkyl and R' is a $C_1$ to $C_{10}$ alkylene. Preferred monomers for use in water-soluble polymers are acrylic acid, vinyl pyrrolidone, vinyl acetate, crotonic acid, methacrylic acid or a combination thereof. Examples of preferred copolymers are the mono ethyl, isopropyl or n-butyl esters of poly(methyl vinyl ether/ maleic acid); poly(vinyl pyrrolidone/vinyl acetate, poly (vinyl pyrrolidone/ethyl methacrylate/methacrylic acid), poly (ethyl acrylate/acrylic acid/N-t-butyl acrylamide), and poly(vinyl acetate/crotonic acid).

Other suitable classes of polymers include anionic, nonionic, amphoteric and cationic polymers. Specific polymers include polyvinylpyrrolidone (PVP), copolymers of PVP and methylmethacrylate, copolymers of PVP and vinyl acetate (VA), polyvinyl alcohol (PVA), copolymers of PVA and crotonic acid, copolymers of PVA and maleic anhydride, hydroxypropyl cellulose, hydroxpropyl guar gum, sodium polystyrene sulfonate, PVP/ethylmethacrylate/methacrylic acid terpolymer and octylacrylamide/acrylate/ butylaminoethyl methacrylate copolymers, and mixtures. A preferred vinyl polymer or copolymer contains at least 50 mole percent of the residues of n-vinyl lactam monomer such as N-vinylpyrrolidinone.

With certain of the acidic water-soluble polymers, it may be necessary to neutralize some acidic groups to promote solubility/dispersibility, e.g., PVA/crotonic acid. Neutralization and increased solubilization are accomplished with one or more inorganic bases such as sodium hydroxide, potassium hydroxide, ammonium hydroxide and/or ammonium carbonate. Among stable organic bases are the water soluble bases such as monoethanolamine (MEA), diethanolamine (DEA), triethanolamine (TEA), 2-methyl-2-amino-1-propanol (AMP), monoamino glycols, and the like, which help solubilize the polymer in water solutions. The level of neutralization required for solubilization varies for each polymer. All of the above-described acidic polymers become soluble in water and hydroalcoholic solutions at 100% neutralization, and all described levels of water/alcohol/ propellant solutions. The pH of these solutions usually ranges from 9 to 12. The lowest neutralization level needed to render the polymer water soluble or dispersible depends on the kind of polymer, and the amount of alcohol, water and propellant. For instance, for poly(methyl vinyl ether/maleic acid) in water the lowest neutralization level is about 40% with sodium hydroxide and AMP; for poly(ethyl acrylate/ acrylic acid/N-t-butyl acrylamide) the lowest neutralization level is about 75% with AMP and 65% with sodium hydroxide. At these neutralization levels, the pH of the solutions range from about 5 to about 7. A slightly acidic or neutral pH such as this is preferred, however, the pH of the formulations of the present invention can vary from about 4 to about 9. Saponification of the ester linkages may occur under alkaline conditions.

The water-soluble polymers may be prepared according to known procedures wherein, for example, a N-vinyl lactam is polymerized, optionally in the presence of one or more other vinyl monomers such as those described above. The N-vinylpyrrolidinone/vinyl acetate copolymers supplied by BASF under the trademark LUVISKOL VA are typical of the water-soluble polymers which may be used in the aerosol hair spray formulations of the present invention. The preferred water-soluble polymers comprise homopolymers of N-vinyl-2-pyrrolidinone and copolymers of N-vinyl-2-pyrrolidinone and up to 50 mole percent vinyl acetate having weight average molecular weights in the range of about 1000 to 100,000. The water-soluble polymers are used at a level of from about 0.5% to about 10% by weight, generally about 1% to about 5% by weight, and preferably from 2% to 4% by weight of the total formulation. The weight average molecular weight of the water-soluble polymers is not critical but is generally in the range from about 1,000 to 2,000,000.

The aerosol formulations also can contain a variety of other nonessential, optional components suitable for rendering such formulations more acceptable. Such conventional optional ingredients are well known to those skilled in the art, e.g., other emulsifiers such as anionics (e.g., sodium alkyl sulfate); preservatives such as benzyl alcohol, methyl paraben, propyl paraben and imidazolidinylurea; cationic emulsifiers/conditioners such as cetyl trimethyl ammonium chloride, stearyl-dimethyl benzyl ammonium chloride, and di(partially-hydrogenated tallow) dimethylammonium chloride; thickeners and viscosity modifiers such as diethanolamide of a long chain fatty acid, fatty alcohols (i.e., cetearyl alcohol), sodium chloride, sodium sulfate, and ethyl alcohol; pH adjusting agents such as citric acid, succinic acid, sodium hydroxide and triethanolamine; coloring agents such as any of the FD&C or D&C dyes; hair oxidizing (bleaching) agents such as hydrogen peroxide, perborate salts and persulfate salts; hair reducing agents such as thioglycolates; perfume oils; chelating agents such as ethylenediaminetetraacetic acid; and among many other agents, polymer plasticizing agents such as glycerin and propylene glycol. These optional materials are generally used individually at a level of from about 0.001% to about 19%, preferably from 0.01% to 5% by weight of the total formulation. It is important to note that the use of cationic emulsifiers in amounts of greater than 1% may precipitate the sulfopolyester, component (1). The aerosol hair-spray formulation of the present invention may also include from about 0.01% to 10%, preferably, 0.1% to 2% by weight of a non-volatile silicone compound or other conditioning agent(s), preferably a water-insoluble, emulsifiable conditioning agent. The preferred non-volatile silicone compound is a polydimethylsiloxane compound, such as a mixture of a low molecular weight polydimethylsiloxane fluid and a higher molecular weight polydimethylsiloxane gum. The non-volatile polydimethylsiloxane compound is added to the formulation of the present invention in an amount sufficient to provide improved combing and improved feel (softness) to the hair after shampooing. Another particularly suitable conditioning agent that can be included in the formulation of the present invention is a volatile hydrocarbon, such as a hydrocarbon including from about 10 to about 30 carbon atoms, that has sufficient volatility to slowly volatilize from the hair after application of the aerosol hair spray formulation. The volatile hydrocarbons provide essentially the same benefits as the silicone conditioning agents.

The preferred volatile hydrocarbon compound is an aliphatic hydrocarbon including from about 12 to about 24 carbon atoms, and having a boiling point in the range of from about 100° C. to about 300° C. Exemplary volatile hydrocarbons are depicted in general structural formula (I), wherein n ranges from 2 to 5,

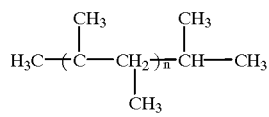

Examples of volatile hydrocarbons useful in the aerosol hair spray formulation of the present invention are the commercially-available compounds PERMETHYL 99A and PERMETHYL 101A, corresponding to compounds of general structure (I) wherein n is 2 and 3, respectively, available from Permethyl Corporation, Frazer, Pa. A volatile hydrocarbon compound is useful in the formulation of the present invention either alone, in combination with another volatile hydrocarbon, or in combination with a volatile silicone. Examples of other suitable water-insoluble conditioning agents that can be incorporated into the hair spray formulations of the present invention include the following: polysiloxane polyether copolymers; polysiloxane polydimethyl dimethylammonium acetate copolymers; acetylated lanolin alcohols; lauryl dimethylamine oxide; a lanolin-derived extract of sterol on sterol esters; lanolin alcohol concentrate; an isopropyl ester of lanolin fatty acids; sulfur rich amino acid concentrates; isopropyl ester of lanolin fatty acids; oleyl alcohol; stearyl alcohol; stearamidopropyl dimethyl myristyl acetate; a polyol fatty acid; a fatty amido amine; guar hydroxypropyltrimonium chloride; cetyl/stearyl alcohol; keratin protein derivatives; isostearamidopropyl dimethylamine; stearamidopropyl dimethylamine; an aminofunctional silicone; isopropyl ester of lanolic acids, ethoxylated (30) castor oil; acetylated lanolin alcohol, fatty alcohol fraction of lanolin, a mineral oil and lanolin alcohol mixture; high molecular weight esters of lanolin; vinylpyrrolidone/dimethylaminoethylmethacrylate copolymer, 5 mole ethylene oxide adduct of soya sterol; 10 mole ethylene oxide adduct of soya sterol; stearic acid ester of ethoxylated (20 mole) methyl glucoside; sodium salt of polyhydroxycarboxylic acid; hydroxylated lanolin; cocamidopropyl dimethylamine lactate; cocamidopropyl dimethylamine propionate; cocamidopropyl morpholine lactate; isostearamidopropyl dimethylamine lactate; isostearamidopropyl morpholine lactate; oleamidopropyl dimethylamine lactate; linoleamidopropyl dimethylamine lactate; stearamidopropyl dimethylamine lactate, ethylene glycol monostearate and propylene glycol mixture; stearamidopropyl dimethylamine lactate; acetamide MEA; lactamide MEA; stearamide MEA; behenalkonium chloride; behenyl trimethyl ammonium methosulfate and cetearyl alcohol mixture; cetearyl alcohol; tallow imidazolinum methoxulfate, stearyl trimonium methosulfate; mixed ethoxylated and propoxylated long chain alcohols; stearamidopropyl dimethylamine lactate, polonitomine oxide; oleamine oxide, stearamide oxide; soya ethyldimonium ethosulfate; ricinolamidopropyl ethyldimonium ethosulfate; N-(3-isostearamidopropyl)-N,N-dimethyl amino glycolate; N-(3-isostearamidopropyl)-N,N-dimethyl amino gluconate; hydrolyzed animal keratin; ethyl hydrolyzed animal keratin; stearamidoethyl diethylamine; cocamidopropyl dimethylamine; lauramidopropyl dimethylamine, oleamidopropyl dimethlamine; palmitamidopropyl dimethylamine; stearamidopropyl dimethylamine lactate; avocado oil; sweet almond oil, grape seed oil; jojoba oil; apricot kernel oil; sesame oil; hydrid safflower oil; wheat germ oil; cocamidoamine lactate; ricinoleamido amine lactate; stearamido amine lactate; stearamido morpholine lactate; isostearamido amine lactate; isostearamido morpholine lactate; wheat germamido dimethylamine lactate; wheat germamidopropyl dimethylamine oxide; disodium isostearamido MEA sulfosuccinate; disodium oleamide PEG-2 sulfosuccinate; disodium oleamide MEA sulfosuccinate; disodium ricinoleyl MEA sulfosuccinate; disodium wheat germamido MEA sulfosuccinate; disodium wheat germamido PEG-2 sulfosuccinate; stearamido amine; stearamido morpholine; isostearamido amine; isostearamido morpholine; polyethylene glycol (400) mono and distearates; synthetic calcium silicate; isostearic alkanolamide; ethyl esters of hydrolyzed animal protein; blend of cetyl and stearyl alcohols with ethoxylated cetyl or stearyl alcohols; amido amines; polyamido amines; propoxylated (1–20 moles) lanolin alcohols; isostearamide DEA; and hydrolyzed collagen protein. Water-insoluble cationic conditioning agents in amounts of less than about 1% may also be used. The use of water-insoluble cationic conditioning agents in amounts of greater than 1% may precipitate the sulfopolyester, component (1). The aqueous formulations of the present invention also can contain the conventional hair spray adjuvants in amounts which generally range from about 0.01 to 2% by weight and preferably 0.1% to 1% by weight. Among the additives which can be used are plasticizers such as glycols, phthalate esters and glycerine; silicones; emollients; lubricants and penetrants such as various lanolin compounds; protein hydrolysates and other protein derivatives; ethylene adducts and polyoxyethylene cholesterol; dyes, tints and other colorants; and perfumes.

Other conventional additives such as preservatives, fragrances, antifoaming agents, hair conditioners, plasticizers, etc. may be added in such quantities as desired, up to about 5.0% by weight of the total formulation. Although the film-forming formulations described herein are particularly useful as aerosol hair sprays for the grooming of hair, it is possible that the formulations, with or without modification, may be used in other types of personal care products. Suitable plasticizers include: Dimethicone Copolyol (Dow Corning 190) at 0.01–0.02%, PEG-6 Capric/Caprylic Glyceride (Softigen 767) at 0.5–2.0%, Diacetin at 1.0–2.0, Lauramide DEA (Monamid 716) at 0.1–1.0%, Phenyl Trimethicone (Abil AV 20-1000) at 0.1–0.2%, propylene glycol at 1.0–5.0%, dipropylene glycol at 1.0–5.0%.

The materials and testing procedures used for the results shown herein are as follows:

DYMEL A (CTFA Adopted Name: Dimethyl Ether) available from DuPont, is a dimethyl ether and is used as a propellant.

LUVISKOL VA 73W PVP/VA (CTFA Adopted Name: PVP/VA Copolymer), available from BASF, is a water-soluble vinyl copolymer of 70 mole percent of N-vinyl-2-pyrrolidone and 30 mole percent of vinyl acetate (50% solid).

SDA-40C is ethanol that has been diluted with ethyl acetate, and is available from Eastman Chemical Company.

Glass transition temperature was determined using a differential scanning calor imeter (DSC).

Inherent viscosity (I.V.) was measured at 23° C. using 0.50 grams of polymer per 100 ml of a solvent consisting of 60% by weight phenol and 40% by weight tetrachloroethane.

Turbidity was measured in NTU's using a model DRT-100B Turbidimeter.

The invention will be further illustrated by a consideration of the following examples, which are intended to b e exemplary of the invention. All parts and percentages in the examples are on a weight basis unless otherwise stated.

EXAMPLE I
Presentation of Water-dispersible Sulfopolyesters A–E.

A round bottom flask equipped with ground-glass head, an agitator shaft, nitrogen inlet and a side arm was charged with isophthalic acid, dimethyl-5-sodiosulfoisophthalate (SIP), diethylene glycol (DEG), and 1,4-cyclohexanedimethanol (CHDM), in the mole percents as set forth below. For comparison purposes, Table I summarizes critical values for each sulfopolyester. A catalyst was added and the flask was immersed in a Belmont bath at 200° C. for one hour under a nitrogen sweep. The temperature of the bath was increased to 230° C. for one hour. The temperature of the bath was increased to 280° C. and the flask was heated for 45 minutes under reduced pressure of 0.5 to 0.1 mm of Hg. The flask was allowed to cool to room temperature and the copolyester was removed from the flask. each sulfopolyester was extruded and pelletized.

More specifically, the composition of each sulfopolyester was as follows:

Sulfopolyester A was prepared with 20.2 mole percent dimethyl-5-sodiosulfoisophthalate and 79.8 mole percent isophthalic acid, and 21.9 mole percent 1,4-cyclohexanedimethanol and 78.1 mole percent diethylene glycol, based on 100 mole percent dicarboxylic acid and 100 mole percent diol. Sulfopolyester A has a Tg of 42° C. and an I.V. of 0.33 dl/g.

Sulfopolyester B was prepared with 22.0 mole percent dimethyl-5-sodiosulfoisophthalate and 78.0 mole percent isophthalic acid, and 23.0 mole percent 1,4-cyclohexanedimethanol and 77.0 mole percent diethylene glycol, based on 100 mole percent dicarboxylic acid and 100 mole percent diol. Sulfopolyester B has a Tg of 47° C. and an I.V. of 0.33 dl/g.

Sulfopolyester C was prepared with 15.6 mole percent dimethyl-5-sodiosulfoisophthalate and 84.4 mole percent isophthalic acid, and 24.2 mole percent 1,4-cyclohexanedimethanol and 75.8 mole percent diethylene glycol, based on 100 mole percent dicarboxylic acid and 100 mole percent diol. Sulfopolyester C has a Tg of 39° C. and an I.V. of 0.29 dl/g.

Sulfopolyester D was prepared with 1.0 mole percent dimethyl-5-sodiosulfoisophthalate and 89.0 mole percent isophthalic acid, and 22.0 mole percent 1,4-cyclohexanedimethanol and 78.0 mole percent diethylene glycol, based on 100 mole percent dicarboxylic acid and 100 mole percent diol. Sulfopolyester D has a Tg of 38° C. and an I.V. of 0.36 dl/g.

Sulfopolyester E was prepared with 18.0 mole percent dimethyl-5-sodiosulfoisophthalate and 82.0 mole percent isophthalic acid, and 46.0 mole percent 1,4-cyclohexanedimethanol and 54.0 mole percent diethylene glycol, based on 100 mole percent dicarboxylic acid and 100 mole percent diol. Sulfopolyester E has a Tg of 55° C. and an I.V. of 0.33 dl/g.

TABLE I

Summary of Sulfopolyester Compositions:

| Sulfopolyester | SIP | CHDM | I.V. | Tg |
|---|---|---|---|---|
| A | 20.2 | 21.9 | 0.33 | 42° C. |
| B | 22.0 | 23.0 | 0.33 | 47° C. |
| C | 15.6 | 24.2 | 0.29 | 39° C. |
| D | 11.0 | 22.0 | 0.36 | 38° C. |
| E | 18.0 | 46.0 | 0.33 | 55° C. |

EXAMPLE II
Preparation of Aerosol Hair Spray Formulations Using the Sulfopolyesters of Example I.

In some examples, ten grams of the sulfopolyester was dispersed in 54.3 grams of distilled water by heating and stirring until a temperature of 75° to 85° C. was reached. After cooling in 40° C. any water lost during heating was replaced and in some cases a water-soluble polymer consisting of 70 mole percent of N-vinyl-2-pyrrolidinone and 30 mole percent of vinyl acetate (50% solids) was added. Ethanol, 35.7 grams as SDA 40C, was added. The mixtures were vacuum filtered through a coarse center glass filter. A preservative, 1-(hydroxymethyl)-5-dimethyl hydantoin, 0.2 grams, was added.

In some examples, ten grams of the sulfopolyester was dispersed in 90 grams of distilled water by heating and stirring until a temperature of 75° to 85° C. was reached. After cooling to 40° C. any water lost during heating was replaced and in some cases a water-soluble polymer consisting of 70 mole percent of N-vinyl-2-pyrrolidinone and 30 mole percent of vinyl acetate (50% solids) was added. The mixtures were vacuum filtered through a coarse center glass filter. A preservative, 1-(hydroxymethyl)-5,5-dimethyl hydantoin, 0.2 grams, was added.

To 65 grams of each of the mixtures was added 42 milliliters of dimethyl ether. The mixtures were sprayed into a glass cuvette which was placed in the Turbidimeter. The turbidity results are listed in Table II.

TABLE II

Turbidity Results (NTU's) Using Sulfopolyesters (A–E)

| Example | A | B | C | D | E |
|---|---|---|---|---|---|
| 7% Sulfopoly 0% EtOH 30% DME | 18.9 | 15.7 | 41.5 | 64.6 | 36.1 |
| 5% Sulfopoly 2% PVP/VA 0% EtOH 30% DME | 19.8 | 15.9 | 41.0 | 63.0 | 33.8 |
| 7% Sulfopoly 25% EtOH 30% DME | 14.0 | 14.0 | 325 | 301 | 981 |
| 5% Sulfopoly 2% PVP/VA 25% EtOH 30% DME | 13.0 | 13.0 | 238 | 205 | 1290 |

The results in Table II clearly indicate that aerosol hair sprays prepared with Sulfopolyesters A and B, which meet the criteria of the present invention, result in clear hair sprays even at 55% volatile organic solvent. The hair sprays prepared with Sulfopolyesters A and B exhibit significantly less than 20 NTU's which is a measure of turbidity. Greater than 20 NTU's is characteristic of a cloudy mixture. Moreover, the presence of a water-soluble polymer in the formulations of the present invention does not deleteriously effect the clarity of the aerosol hair spray formulations. In contrast, the addition of alcohol to hair spray formulations prepared with Sulfopolyesters C, D, or E result in extremely cloudy hair spray formulations with as little as 30% volatile organic solvent.

EXAMPLE III
Curl Retention Evaluation of Aerosol Hair Sprays.

The aerosol hair spray prepared from Sulfopolyesters B and D of Example II and LUVISKOL VA 73W PVP/VA were sprayed on a tress for ten seconds. Testing was done on natural brown, European virgin hair tresses in which about two grams of hair, root end, were glued to a 2" by 2" plastic tab. The tresses were cut so that the length of hair hanging below the tabs was six inches. Prior to applying the aerosol hair spray, the tresses had been washed with a nonconditioning shampoo, placed in ethanol bath for 15 minutes, rinsed with deionized water, wrapped around a one inch diameter curler while wet, and placed in an oven at 45° C. to dry. The tresses were removed from the oven and allowed to cool to room temperature.

The tresses were hung in a humidity chamber at 25° C. and 80% relative humidity. The curl loss or droop was determined over a one hour period in ten minute intervals. The test results are listed in Table III.

TABLE III

Curl Retention Evaluation of Aerosol Hair Sprays
Time (minutes)

| Polymer | 0 | 10 | 20 | 30 | 40 | 50 | 60 |
|---|---|---|---|---|---|---|---|
| Sulfo poly B | 100 | 100 | 98.1 | 96.5 | 96.5 | 95.2 | 95.2 |
| Sulfo Poly D | 100 | 91.4 | 88.9 | 84.3 | 84.3 | 84.3 | 84.3 |
| PVP/VA | 100 | 79.8 | 74.3 | 70.4 | 67.2 | 67.2 | 67.2 |

The test results in Table III indicate that aerosol hair sprays prepared using the critical ranges of the present invention clearly are superior in maintaining curl retention as compared to aerosol hair sprays that fall outside the critical ranges. In addition, the data indicates that the use of water-soluble PVPNVA polymers without the sulfopolyesters of the present invention result in poor curl retention and poor humidity resistance.

Many variations will suggest themselves to those skilled in this art in light of the above detailed description. All such obvious modifications are within the full intended scope of the appended claims.

All of the aforementioned Patents and Patent Application are incorporated herein by reference in their entirety.

What is claimed is:

1. A clear aerosol hair spray composition exhibiting less than 20 NTU's comprising a water/alcohol liquid vehicle, a propellant, and a sulfopolyester containing 20 to 26 mole percent dimethyl-5-sodiosulfoisophthalate and 74 to 80 mole percent isophthalic acid, based on 100 mole percent dicarboxylic acid, as a dicarboxylic acid component, and 10 to 30 mole percent 1,4-cyclohexanedimethanol and 70 to 90 mole percent diethylene glycol, based on 100 mole percent diol, as a diol component, said sulfopolyester having a Tg of about 42° C. to 50° C. and an inherent viscosity of 0.24 to 0.60 dl/g.

2. The composition according to claim 1 wherein the total amount of alcohol and propellant present in the composition is not greater than 60 weight percent, based on the weight of the composition.

3. The composition according to claim 1 wherein the alcohol is present in an amount of 20 to 30 weight percent based on the weight of the composition.

4. The composition according to claim 1 wherein the alcohol is an aliphatic straight or branched chain monohydric alcohol having 2 to 4 carbon atoms.

5. The composition according to claim 2 wherein the alcohol is ethanol.

6. The composition according to claim 1 wherein the propellant is selected from the group consisting of $C_1$ to $C_4$ aliphatic hydrocarbons and dimethyl ether.

7. The composition according to claim 6 wherein the propellant is dimethyl ether.

8. The composition according to claim 1 wherein the sulfopolyester is present in an amount of 0.5 to 15 weight percent, based on the weight of the composition.

9. The composition according to claim 1 wherein the propellant is present in an amount of from about 3 to about 40 weight percent, based on the weight of the composition.

10. The composition according to claim 1 further comprising a water-soluble polymer that is soluble in the water/alcohol liquid vehicle.

11. The composition according to claim 10 wherein the water-soluble polymer contains at least one, or more, vinyl or acrylate monomers selected from the group consisting of alkyl vinyl ethers, alkyl acrylates, vinyl esters, N-vinyl lactams, alkyl acrylamides, half vinyl esters/half amides, half esters of maleic anhydride, vinyl pyrrolidone, acrylic acid, crotonic acid, and methacrylic acid.

12. The composition according to claim 11 wherein the water-soluble polymer is a copolymer of N-vinyl 2-pyrrolidone and vinyl acetate.

13. The composition according to claim 11 wherein the water-soluble polymer is selected from the group consisting of anionic, nonionic, and amphoteric polymers.

14. The composition according to claim 11 wherein the water-soluble polymer is present is an amount of from about 0.5 to about 10 weight percent, based on the weight of of the composition.

15. The composition according to claim 1 further comprising a plasticizer.

16. The composition according to claim 1 further comprising a perfume.

17. The composition according to claim 5 wherein the propellant is dimethyl ether.

18. The composition according to claim 17 further comprising a water-soluble polymer that is soluble in the water/ethanol liquid vehicle.

19. The composition according to claim 18 wherein the water-soluble polymer is a copolymer of N-vinyl-2-pyrrolidone and vinyl acetate.

* * * * *